United States Patent [19]

Leugers

[11] Patent Number: 4,622,853
[45] Date of Patent: Nov. 18, 1986

[54] LASER INDUCED ACOUSTIC GENERATION FOR SONIC MODULUS

[75] Inventor: Mary A. Leugers, Midland, Mich.

[73] Assignee: Union Camp Corporation, Wayne, N.J.

[21] Appl. No.: 768,910

[22] Filed: Aug. 23, 1985

[51] Int. Cl.$^4$ .......................... G01N 29/00; D21F 7/00
[52] U.S. Cl. ........................................ 73/597; 73/159; 73/643
[58] Field of Search .......................... 73/597, 643, 159

[56] References Cited

U.S. PATENT DOCUMENTS

| | | | |
|---|---|---|---|
| 4,255,971 | 3/1981 | Rosencwaig | 73/643 |
| 4,276,780 | 7/1981 | Patel et al. | 73/643 |
| 4,291,577 | 9/1981 | Baum et al. | 73/597 |
| 4,574,634 | 3/1986 | Pappano | 73/597 |

OTHER PUBLICATIONS

Scruby et al., "A Laser-Generated Standard Acoustic Emission Source", *Materials Evaluation* 39, Dec. 1981, pp. 1250-1254.

Primary Examiner—Stewart J. Levy
Assistant Examiner—John E. Chapman, Jr.
Attorney, Agent, or Firm—Kane, Dalsimer, Kane, Sullivan and Kurucz

[57] ABSTRACT

A method and device which measures the velocity of ultrasonic waves in a moving web is disclosed. The excitation source is a laser or other device which produces short intense light pulses and the detection system is either a piezoelectric transducer or a microphone. The latter obviates any need for physical contact with the web in order to carry out tests for strength parameters as the web is manufactured.

3 Claims, 2 Drawing Figures

LASER INDUCED ACOUSTIC GENERATION FOR SONIC MODULUS

BACKGROUND OF THE INVENTION

1. Field of the Invention

This invention relates to a method and apparatus for the non-destructive measurement of physical properties of a web or sheet, particularly of paper.

2. Brief Description of the Prior Art

Paper manufactured for various applications and needs, must meet certain strength requirements. Such strength parameters are usually determined by tests which in the process destroys the sample being tested, for example, by the application of stress until the paper tears. This kind of destructive testing is obviously undesirable in some circumstances. For example, these tests may be performed on paper that has been wound on a reel. It must be cut from the reel and is usually conditioned to a standard moisture prior to being tested. This process requires considerable time, which is undesirable for a test method used to control a paper machine since considerable off-quality product can be produced prior to detection and correction.

U.S. Pat. No. 4,291,577 describes a method and apparatus for the non-destructive testing of paper as it is produced in a continuous fast moving web. The invention utilizes the known fact that many of the strength parameters of paper are related to Young's modulus of elasticity. The latter can be correlated with the velocity of sound waves traveling through the paper web. A transmitting transducer sends a mechanical signal to the paper and a receiving transducer picks up the ultrasound signal from the paper. By knowing the time it takes the ultrasonic waves to travel through the paper and the distance they travel the velocity of the ultrasonic waves can be calculated. The transducers are located in wheels which are in physical contact with the moving paper web. While the testing may be carried on in a non-destructive way while the paper is being produced, such a device is inherently complex. Thus, the wheels containing the sending and receiving transducers must be highly synchronized. The sending transducer must contact the sheet and produce an acoustic wave which must be detected 1 to 100 microseconds later at some receiving transducer a short distance away. The receiving transducer must remain in contact with the sheet long enough so that it will not miss the first oscillation of the acoustic pulse which has been generated. These are serious impediments to the test method.

More importantly, the signal strength depends on the force with which mechanical sending and receiving transducers are applied to the moving web. This factor alone is a serious impediment to the use of the method, creating stress forces on both the apparatus and the moving web.

Obviously it would be desirable to develop a method and apparatus which would test paper non-destructively, in the absence of physical contact or with minimal force applied to the web. The present invention answers the need for such an invention, by utilizing a laser beam for exciting the necessary acoustic signal in the web, thus eliminating one point of physical contact. The receiver can either be a mechanical transducer in contact with the paper or a microphone not in physical contact with the paper, thus minimizing or in the case of a microphone, eliminating points of physical contact and stress.

The use of laser beams to generate acoustic waves is described in U.S. Pat. No. 4,169,662.

SUMMARY OF THE INVENTION

The invention comprises a method and a device for non-destructively testing a physical property of a workpiece such as a moving web of paper.

In one embodiment, a beam of laser light or other short light pulse producing device is used for excitation of an acoustic wave and a microphone is used as the means of detecting the velocities of the ultrasound waves generated. This enables the on-line testing of a moving web in the absence of physical contact with the web. In another embodiment, a piezoelectric transducer is used as a means of detection.

BRIEF DESRIPTION OF THE DRAWINGS

DETAILED DESCRIPTION OF THE INVENTION

The method of the invention may be used to measure strength characteristics of a wide variety of light absorbing test materials including, but not limited to, sheets or webs of paper, synthetic polymeric resins and the like.

According to one embodiment of the method of the present invention, a paper web as it is being manufactured, on a papermaking machine is subjected to short pulses of light, preferably laser radiation, for the purpose of determining mechanical strength properties of the paper. The molecules in the paper which absorb the incident photons, re-emit the energy through several channels, the most efficient of which is by a localized heat pulse in the sample. Heat thus produced in turn generates mechanical stress in the structure of the material which manifests itself as an acoustic wave. The acoustic wave propagates from the illuminated point outward through the medium. The acoustic pulse generated may be detected at varying distances away from the point of generation to obtain a measurement of the acoustic velocity in the medium.

The initial degree of excitation achieved with the light source depends on the wavelength used. Convenient wavelengths lie in the range from about 200 to about 10,000 nm. Use of optimal wavelengths within this range results in a greater absorption of the incident energy, and therefore for a stronger acoustical signal. Any known light source producing the desired effect may be used, preferably a laser source. The measurements of longitudinal and shear wave velocities propagated throughout the paper web can then be related to the Young's moduli, shear moduli, and Poisson's ratios for paper. This type of on-line determination can be used in a closed-loop control system to adjust and optimize paper machine variables, such as rush-drag ratio, level of refining, wet pressing, etc. during manufacture of the paper web.

The measurement of the velocity of the acoustic waveform may also be used to obtain information regarding the interaction of the waveform with the medium through which it traveled such as, the density of the medium, as well as the orientation of various microscopic elements in the medium.

Figure 1:
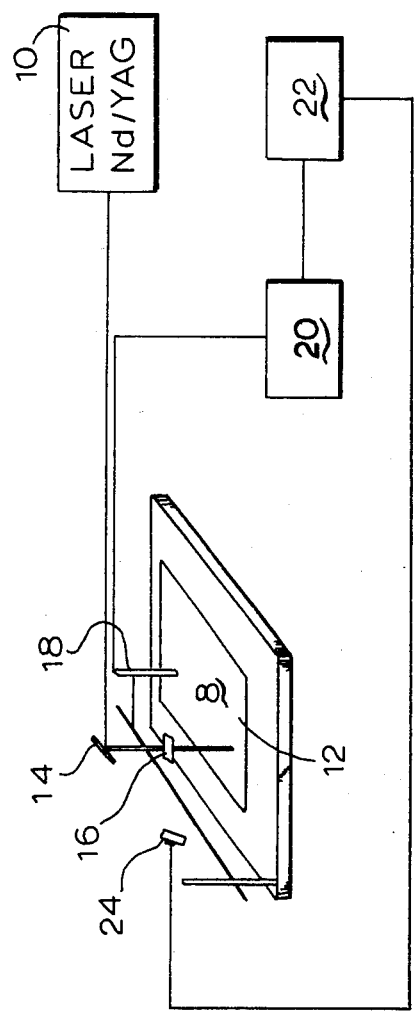
FIG. 1 is a schematic view of the design of a device of the invention using laser light as a source of excitation and a piezoelectric transducer as a means of detection.

In one embodiment of this invention, the excitation of the acoustic waveform is carried out with a beam of laser light and detection of the sonic waves is achieved with a piezoelectric transducer which makes brief physical contact with the web of paper. This embodiment is schematically illustrated in the drawing of FIG. 1. A source of laser light of 532 nm wavelength from a Neodymium/Yttrium-Aluminum-Garnet (Nd/YAG) laser 10 is directly focused onto the absorbing surface 12 of paper 8 by reflection from a mirror 14 and condensation through a lens 16 (the lens is optional). The source of light 10 might also be any other device which produces short intense light pulses on the order of one microsecond or less such as a flash lamp. The detection probe, which is in this case a piezoelectric transducer 18, is placed in contact with the surface 12 of paper 8 at a fixed and pre-determined distance from the point of impingement of the laser beam. In the embodiment shown in FIG. 1, the detection system consists of the piezoelectric transducer 18, the pre-amplifier 20, a transient digitizer 22 and a photodiode 24.

As shown in FIG. 1, the acoustic signal picked up by the transducer 18 is converted to an electrical signal, and transmitted to the amplifier 20. The amplified signal is then transmitted to the transient digitizer 22. The transient digitizer 22 measures the time between the firing of the laser as detected by the photodiode 24 and the reception of the electrical signal by the transducer 18. The time measured includes electrical transmission time in electrical cables, etc., but this added time may be calculated and subtracted to obtain the transmission time of the acoustic wave through the test material 8. The measured transmission time of the acoustic wave may be averaged and used to calculate Young's modulus of elasticity and to determine the strength properties of the sheet 8.

In a preferred embodiment of the invention, the detection system uses a microphone in an acoustically baffled housing in place of the piezoelectric transducer 18 thus obviating the need for any physical contact with the paper 8.

In the following examples, the acoustic signals produced by excitation of the paper with a laser beam were analyzed with a piezoelectric system as shown in FIG. 1. The excitation source was a Quanta-Ray Nd/YAG laser, which produces a fundamental wavelength of 1064 nm, with a pulse duration of approximately 10 nanoseconds. This frequency is doubled to produce a pulse of 532 nm radiation. This short pulse of light is directed onto a sheet of paper to populate various acoustic modes in the paper.

EXAMPLE 1

This example shows a comparison of longitudinal wave velocities set up in four standard materials when the signal is induced with a contacting piezoelectric transducer of the type previously known and when the signal is induced with the use of the laser according to the present invention. The data obtained indicate that the laser produces substantially identical results without having contacted the sheet.

| SAMPLE NO. | SAMPLE TYPE | LONGITUDINAL WAVE VELOCITY (MM/μ SEC) | |
|---|---|---|---|
| | | LASER INDUCTION | PIEZOELECTRIC TRANSDUCER INDUCTION |
| 1. | Black Linear High Density Polyethylene | 1.96 | 1.97 |
| 2. | White Linear High Density Polyethylene | 1.73 | 1.83 |
| 3. | UV Stabilized Polystyrene | 2.08 | 2.16 |
| 4. | Acrylic | 2.27 | 2.33 |

EXAMPLE 2

In this example a comparison is made between longitudinal wave velocities generated by the previously described method (U.S. Pat. No. 4,291,577) of a contacting piezoelectric transducer and a non-contacting laser according to the present invention on five samples of various types of paper. Excellent correspondence is achieved and the breadth of the invention to cover different classes of paper including: unbleached products, fine paper products, commercial linerboard products and laboratory test sheets is demonstrated.

| SAMPLE NO. | SAMPLE TYPE | LONGITUDINAL WAVE VELOCITY (MM/μ SEC) | |
|---|---|---|---|
| | | LASER INDUCTION | PIEZOELECTRIC TRANSDUCER INDUCTION |
| 5. | 44 Kappa Pine Pulp Handsheet (A) | 3.30 | 3.48 |
| 6. | Commercial Linerboard (Machine Direction) | 3.36 | 3.33 |
| 7. | Commercial Cardboard (Cross Direction) | 1.94 | 2.05 |
| 8. | White Continuous Forms Paper (Machine Direction) | 3.51 | 3.63 |

EXAMPLE 3

It is well known that the velocity of sound travels at different rates in a commercially produced sheet of paper in the direction aligned with the paper machine axis relative to the direction across the paper machine axis. Example 3 demonstrates that the ratio of the velocity in the machine direction to the cross machine direction is accurately predicted for commercial papers when the non-contacting laser device of the present invention is used and that this value corresponds to that obtained by the previous contacting piezoelectric transducer.

| SAMPLE NO. | SAMPLE TYPE | LONGITUDINAL WAVE VELOCITY RATIO (MACHINE DIRECTION) (CROSS MACHINE DIRECTION) | |
|---|---|---|---|
| | | LASER INDUCTION | PIEZOELECTRIC TRANSDUCER INDUCTION |
| 6. | Commercial | 1.50 | 1.41 |

| SAMPLE NO. | SAMPLE TYPE | LONGITUDINAL WAVE VELOCITY RATIO (MACHINE DIRECTION) (CROSS MACHINE DIRECTION) | |
|---|---|---|---|
| | | LASER INDUCTION | PIEZOELECTRIC TRANSDUCER INDUCTION |
| 7. | Linerboard Commercial Cardboard | 1.59 | 1.63 |
| 8. | White Continuous Forms Paper | 1.41 | 1.36 |

EXAMPLE 4

To calculate the meaningful modulus properties in a sheet of paper requires transmission and detection of both longitudinal wave velocities and shear wave velocities. Example 4 demonstrates that the non-contacting laser device of the present invention is capable of measuring and detecting both longitudinal and shear waves in agreement with those generated and detected by the prior art contacting piezoelectric transducer device.

| SAMPLE NO. | SAMPLE TYPE | SHEAR WAVE VELOCITY (mm/μ SEC) | |
|---|---|---|---|
| | | LASER INDUCTION | PIEZOELECTRIC TRANSDUCER INDUCTION |
| 4. | Acrylic | 2.27 | 2.33 |

EXAMPLE 5

For a test method to have value the data must be reproducible and precise. Example 5 demonstrates that good reproducibility can be achieved in independent tests with the laser system on a variety of materials.

| SAMPLE NO. | SAMPLE TYPE | LASER INDUCED LONGITUDINAL WAVE VELOCITY (mm/μSEC) | |
|---|---|---|---|
| | | Test 1 | Test 2 |
| 1. | Black Linear High Density Polyethylene | 1.95 | 1.97 |
| 2. | White Linear High Density Polyethylene | 1.75 | 1.72 |
| 3. | UV Stabilized Polystyrene | 2.04 | 2.11 |
| 6. | Commercial Linerboard (Machine Direction) | 3.51 | 3.20 |
| 6. | Commercial Linerboard | 2.21 | 2.26 |

| SAMPLE NO. | SAMPLE TYPE | LASER INDUCED LONGITUDINAL WAVE VELOCITY (mm/μSEC) | |
|---|---|---|---|
| | | Test 1 | Test 2 |
| | (Cross Machine Direction) | | |

EXAMPLE 6

Figure 2:
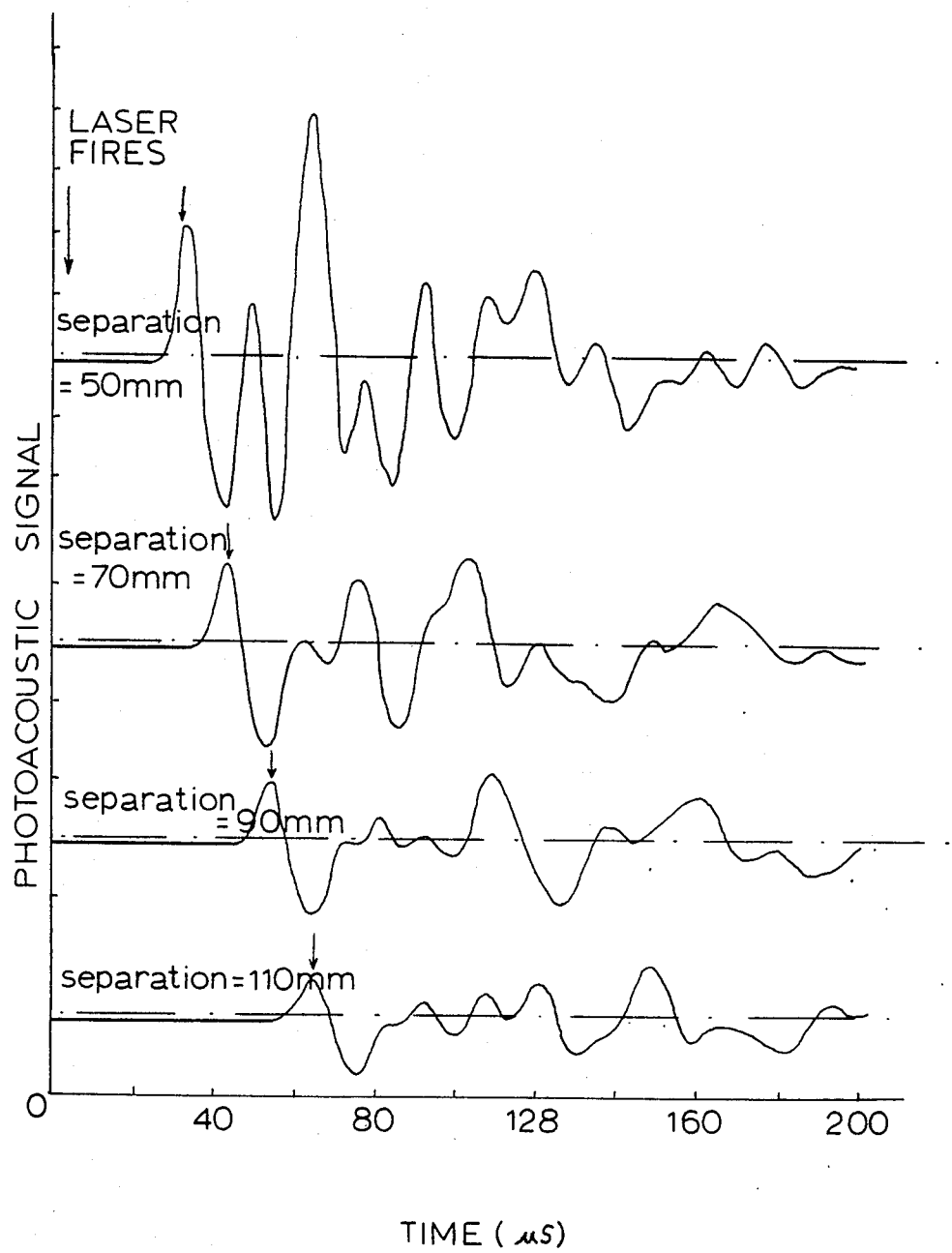
FIG. 2 shows photoacoustic waveforms obtained in paper with varying distance between excitation and detection points.

The procedure of Example 1, sample No. 1, supra, is repeated except that the distance separating the point of laser beam impingement and the transducer reception of the generated acoustic wave is varied. The waveform produced in each instance together with separation distance is given in FIG. 2 of the accompanying drawings.

EXAMPLE 7

The procedure of Examples 1-5, supra, is repeated except that in this set of experiments the piezoelectric transducer 18 is replaced with a microphone in an acoustically baffled housing. The laser sends a pulse of light to the test sheet and an electrical pulse is sent to a trigger simultaneously. The electrical pulse triggers the transient digitizer 22 to begin recording signals from the microphone. This photoacoustic signal is received at the microphone and averaged several times to produce a waveform like those illustrated in FIG. 2 of the accompanying drawings.

What is claimed:

1. A method of non-destructively testing, free of physical contact, a physical property of a moving web or sheet of paper, which comprises;
    beaming a source of short light pulses and amplitudes at said moving web or sheet; and
    measuring the velocity of the ultrasonic waves produced in the web or sheet by the thermal effect induced by the light pulses.

2. A method for non-destructively testing a physical property of a moving web or sheet of paper, which comprises;
    beaming a source of short light pulses on said moving web or sheet; and
    detecting the ultrasound velocities responsive to the thermal effect induced by the light pulses by means of a piezo-electric transducer which makes physical contact with the moving web or sheet of paper.

3. In a method of non-destructively testing a physical property of a light absorbing, moving web of paper, the improvement whereby all physical contact with the web is eliminated, comprising:
    beaming a source of short light pulses at said light absorbing moving web; and
    detecting the ultrasound velocities responsive to the thermal effect induced by the light pulses.

* * * * *